US009278080B2

(12) United States Patent
Kostadinov et al.

(10) Patent No.: US 9,278,080 B2
(45) Date of Patent: *Mar. 8, 2016

(54) COMPOSITIONS AND METHODS FOR INHIBITING GASTRIC ACID SECRETION

(75) Inventors: Aleksey Kostadinov, Rehovot (IL); Ayelet David, Omer (IL); Sabina Glozman, Naharya (IL)

(73) Assignee: Vecta, Ltd., Ramat Gan (IL)

( * ) Notice: Subject to any disclaimer, the term of this patent is extended or adjusted under 35 U.S.C. 154(b) by 15 days.

This patent is subject to a terminal disclaimer.

(21) Appl. No.: 12/768,375

(22) Filed: Apr. 27, 2010

(65) Prior Publication Data

US 2010/0247634 A1    Sep. 30, 2010

Related U.S. Application Data

(63) Continuation of application No. 11/191,688, filed on Jul. 27, 2005, now Pat. No. 7,803,817.

(60) Provisional application No. 60/679,664, filed on May 11, 2005.

(51) Int. Cl.
*A61K 31/19* (2006.01)
*A61K 9/20* (2006.01)
*A61K 31/4439* (2006.01)
*A61K 47/12* (2006.01)

(52) U.S. Cl.
CPC ............. *A61K 31/19* (2013.01); *A61K 9/2081* (2013.01); *A61K 31/4439* (2013.01); *A61K 47/12* (2013.01)

(58) Field of Classification Search
CPC .......... A61K 2300/00; A61K 31/4439; A61K 47/12; A61K 9/2081
See application file for complete search history.

(56) References Cited

U.S. PATENT DOCUMENTS

| | | | |
|---|---|---|---|
| 2,343,011 A | 2/1944 | Huppert | |
| 4,255,431 A | 3/1981 | Junggren et al. | |
| 4,716,153 A | 12/1987 | Morishita et al. | |
| 4,758,579 A | 7/1988 | Kohl et al. | |
| 4,767,627 A | 8/1988 | Caldwell et al. | |
| 4,786,505 A * | 11/1988 | Lovgren et al. ............... | 424/468 |
| 4,853,230 A | 8/1989 | Lovgren et al. | |
| 5,093,738 A | 3/1992 | Watanabe et al. | |
| 5,137,729 A | 8/1992 | Kuroya et al. | |
| 5,238,686 A | 8/1993 | Eichel et al. | |
| 5,559,152 A | 9/1996 | Komissarova et al. | |
| 5,626,875 A | 5/1997 | Ballester Rodes et al. | |
| 5,731,002 A * | 3/1998 | Olovson et al. ............... | 424/484 |
| 5,750,531 A | 5/1998 | Lee et al. | |
| 5,800,832 A | 9/1998 | Tapolsky et al. | |
| 5,840,737 A | 11/1998 | Phillips | |
| 5,972,389 A * | 10/1999 | Shell et al. ............... | 424/501 |
| 6,093,738 A | 7/2000 | Karimian et al. | |
| 6,132,768 A | 10/2000 | Sachs et al. | |
| 6,136,344 A | 10/2000 | Depui et al. | |
| 6,159,498 A | 12/2000 | Tapolsky et al. | |
| 6,228,400 B1 | 5/2001 | Lee et al. | |
| 6,284,271 B1 * | 9/2001 | Lundberg et al. ............... | 424/466 |
| 6,296,876 B1 | 10/2001 | Odidi et al. | |
| 6,328,993 B1 * | 12/2001 | Linder et al. ............... | 424/451 |
| 6,350,468 B1 | 2/2002 | Sanso | |
| 6,489,346 B1 | 12/2002 | Phillips | |
| 6,645,988 B2 | 11/2003 | Phillips | |
| 6,699,885 B2 | 3/2004 | Phillips | |
| 6,780,882 B2 | 8/2004 | Phillips | |
| 6,815,414 B2 | 11/2004 | Chowers et al. | |
| 7,211,568 B2 | 5/2007 | Liu et al. | |
| 7,271,146 B2 | 9/2007 | Glozman | |
| 7,803,817 B2 * | 9/2010 | Kostadinov et al. ............ | 514/333 |
| 7,918,908 B2 | 4/2011 | Nahey et al. | |
| 7,981,908 B2 | 7/2011 | Kostadinov et al. | |
| 2001/0020005 A1 | 9/2001 | Chowers et al. | |
| 2003/0049204 A1 | 3/2003 | Leyland-Jones | |
| 2003/0175360 A1 | 9/2003 | Luzatti | |
| 2003/0235628 A1 | 12/2003 | Taneja et al. | |
| 2004/0067875 A1 | 4/2004 | Lai et al. | |
| 2004/0106634 A1 | 6/2004 | Satoh et al. | |
| 2004/0248942 A1 | 12/2004 | Hepburn et al. | |
| 2005/0112213 A1 | 5/2005 | McCullough | |
| 2005/0181052 A1 | 8/2005 | Patel et al. | |
| 2005/0232992 A1 | 10/2005 | Devane et al. | |

(Continued)

FOREIGN PATENT DOCUMENTS

| | | |
|---|---|---|
| CN | 1122109 A | 5/1996 |
| EP | 05129 A1 | 10/1979 |
| EP | 124495 A2 | 11/1984 |
| EP | 166287 A1 | 1/1986 |
| EP | 174726 A1 | 3/1986 |

(Continued)

OTHER PUBLICATIONS

Talpes et al. (International Journal of Clinical Pharmacological Therapy, Jan. 2005, vol. 43, pp. 51-56).*
Hunt et al (Journal of Physiology, 1973, vol. 230, pp. 171-184).*
Kuroda et al (Archives of International Pharmacodynamic Therapy, 1977, vol. 226, pp. 324-330).*

(Continued)

*Primary Examiner* — Sean Basquill
*Assistant Examiner* — Mark V Stevens
(74) *Attorney, Agent, or Firm* — Cooley LLP; Ivor R. Elrifi; Christina K. Stock

(57) ABSTRACT

The present invention is related to novel oral compositions comprising an irreversible gastric H+/K+-ATPase proton pump inhibitor (PPI) as a gastric acid secretion inhibitor and one or more small carboxylic acid molecules as parietal cell activators in the gastric lumen. Unexpectedly, the compositions of the present invention are capable of enhancing the anti-acid activity of PPI in the stomach. The present invention further relates to a method of using such compositions to reduce gastric acid secretion in a mammal.

11 Claims, 3 Drawing Sheets

(56) References Cited

U.S. PATENT DOCUMENTS

| | | |
|---|---|---|
| 2005/0239845 A1 | 10/2005 | Proehl et al. |
| 2005/0244538 A1 | 11/2005 | Andersen et al. |
| 2006/0127489 A1 | 6/2006 | Crothers et al. |
| 2006/0135406 A1 | 6/2006 | Glozman et al. |
| 2006/0183779 A1 | 8/2006 | Brauns et al. |
| 2006/0210604 A1 | 9/2006 | Dadey et al. |
| 2006/0257467 A1 | 11/2006 | Kostadinov et al. |
| 2009/0274766 A1 | 11/2009 | Marash et al. |
| 2009/0304790 A1 | 12/2009 | Nilsson et al. |
| 2010/0247634 A1 | 9/2010 | Kostadinov et al. |
| 2011/0111039 A1 | 5/2011 | Kostadinov et al. |
| 2011/0250268 A1 | 10/2011 | Kostadinov et al. |

FOREIGN PATENT DOCUMENTS

| | | |
|---|---|---|
| EP | 259174 A1 | 3/1988 |
| EP | 322133 A1 | 6/1989 |
| EP | 404322 A1 | 12/1990 |
| EP | 0696921 B1 | 2/1996 |
| EP | 1087783 A2 | 4/2001 |
| EP | 1917959 A1 | 5/2008 |
| GB | 2163747 A | 3/1986 |
| GB | 2394895 A | 5/2004 |
| JP | 60193917 | 10/1985 |
| JP | 2005519901 A | 7/2005 |
| RU | 2205028 C2 | 5/2003 |
| RU | 2240110 C2 | 11/2004 |
| WO | WO-9006925 A1 | 6/1990 |
| WO | WO-9113337 A1 | 9/1991 |
| WO | WO-9119711 A1 | 12/1991 |
| WO | WO-9119712 A1 | 12/1991 |
| WO | WO-9401099 A1 | 1/1994 |
| WO | WO-9427988 A1 | 12/1994 |
| WO | WO-9501977 A1 | 1/1995 |
| WO | WO-9725030 A1 | 7/1997 |
| WO | WO-9965513 A2 | 12/1999 |
| WO | WO-0078293 A1 | 12/2000 |
| WO | WO-0122985 A1 | 4/2001 |
| WO | WO-0151050 A1 | 7/2001 |
| WO | WO 03/061584 A2 | 7/2003 |
| WO | WO-03086267 A2 | 10/2003 |
| WO | WO 2004112756 A1 * | 12/2004 |
| WO | WO-2005020879 A2 | 3/2005 |
| WO | WO 2005065664 A1 * | 7/2005 |
| WO | WO-2005065664 A1 | 7/2005 |
| WO | WO 2006/037342 A2 | 4/2006 |
| WO | WO-2006120500 A1 | 11/2006 |
| WO | WO-2008012621 A2 | 1/2008 |

OTHER PUBLICATIONS

Ammar et al., "Syntaxin 3 is required for cAMP-induced acid secretion: streptolysin O-permeabilized gastric gland model", *Am. J. Physiol.—Gastrointestinal Liver Physiol.*, 282:G23-G33 (2002).
Ayalon et al., "Does Luminal Gastrin Stimulate Gastric Acid Secretion?", *Am. J. Surg.*, 141:94-97 (1981).
Chand et al., "Sleep dysfunction in patients with gastro-oesophageal reflux disease: prevalence and response to GERD therapy, a pilot study", *Aliment Pharmacol. Ther.* 2004, 20:969-974 (2004).
Chen et al., "Sleep Symptoms and Gastroesophageal Reflux", *J. Clin. Gastroenterol.*, 42(1):13-17 (2008).
De Graef et al., "Influence of the Stimulation State of the Parietal Cells on the Inhibitory Effect of Omeprazole on Gastric Acid Secretion in Dogs," Gastroenterology, 91:333-337 (1985).
European Examination Report, Application No. 07804623.2 Feb. 9, 2010.
Fiddian-Green et al., "A physiological role for luminal gastrin?" *Surgery*, 83(6):663-668 (1978).
Hatlebakk et al., "Pharmacokinetic Optimisation in the Treatment of Gastro-Oesophageal Reflux Disease", *Clin. Pharmacokinet.*, 31(5):386-406 (1996).
Hunt et al., "The Effect of Citric Acid and Its Sodium Salts in Test Meals on the Gastric Outputs of Acid and of Chloride", *J. Physiol.*, 230(1):171-184 (1973).
International Search Report for PCT/IB05/02223 dated Mar. 28, 2006.
International Search Report for PCT/IB07/01078 dated Apr. 9, 2009.
International Search Report from PCT/IB2009/006176 dated Dec. 8, 2009.
Kuroda et al., "Inhibitory Effect of Fumaric Acid and Dicarboxylic Acids on Gastric Ulceration in Rats", *Arch. Mt. Pharmacodyn.*, 226:324-330 (1977).
Maliuk et al, "Effect of Succinate Sodium on the Acid Forming and Motor Function of the Stomach in Patients with Tuberculosis", *rachebnoe Delo*, 10:60-62 (1981) (Abstract Only).
Merritt, A.M., "The Equine Stomach: A Personal Perspective (1963-2003)", 49th Annual Convention of the American Association of Equine Practitioners, www.ivis.org, Nov. 21, 2003.
Morii et al., "The Potency of Substituted Benzimidazoles such as E3810, Omeprazole, Ro 18-5364 to Inhibit Gastric $H^+,K^+$-ATPase is Correlated with the Rate of Acid-Activation of the Inhibitor", *Biochem. Pharmacol.*, 39(4):661-667 (1990).
Morrell et al., "Absorption of Pentagastrin from Gastrointestinal Tract in Man," *Lancet*, 2(7937):712 (1975) (Abstract Only).
Nagata et al., "Inhibitory Action of Lansoprazole and Its Analogs Against *Helicobacter pylori*: Inhibition of Growth is Not Related to Inhibition of Urease," *Antimicrobial Agents and Chemotherapy*, 39(2):567-570 (1995).
Nobuhara et al., "Vinegar is a Dietary Mild Irritant to the Rat Gastric Mucosa", *Japanese J. Pharmacol.*, 41:101-108 (1986).
Pokrovsky et al., "On the Role of Succinate in Energy Supply of the Hydrochloric Acid Secretion in the Gastric Mucosa", *J. Physiol.*, 10:1567-1573 (1973) (English Abstract Only).
Sachs, G., "Improving on PPI-based therapy of GORD", *Eur. J. Gastroenterol. Hepatol.*, 13(Suppl. 1):S35-S41(2001).
Scarpignato et al., "Acid Suppression Therapy: Where Do We Go from Here?" Dig. Dis., 24:11-46 (2006).
Shaker et al., "Nighttime Heartburn Is an Under-Appreciated Clinical Problem That Impacts Sleep and Daytime Function: The Results of a Gallup Survey Conducted on Behalf of the American Gastroenterological Association", *Am. J. Gastroenterol.*, 98(7):1487-1493 (2003).
Teyssen et al., "Maleic acid and succinic acid in fermented alcoholic beverages are the stimulants of gastric acid secretions", *J. Clin. Invest.*, 103(5):707-713 (1999).
Teyssen et al., "Maleic and Succinic Acid as Stimulants of Acid Production in Isolated Native Rat Gastric Parietal Cells", *Esophageal, Gastric and Duodenal Disorders*, G1456:A333 (Apr. 1999).
Tytgat, G.N., "Shortcomings of the first-generation proton pump inhibitors", *Eur. J. Gastroenterol. Hepatol.*, 13(Suppl. 1):S29-S33 (2001).
Written Opinion of the International Search Authority for PCT/IB07/01078 dated Apr. 9, 2009.
Written Opinion of the International Search Authority for PCTIB05/02223 dated Mar. 28, 2006.
Yau et al., "A comparison of omeprazole and ranitidine for prophylaxis against aspiration pneumonitis in emergency Caesarean section", *Anaesthesia*, 47:101-104 (1992).
Martindale. "Supplementary Drugs and Other Substances." Parfitt, ed. London: The Pharmaceutical Press. Thirty-second ed. (1999):1616.
Postius et al. "The Novel Proton Pump Inhibitor Pantoprazole Elevates Intragastric pH for a Prolonged Period When Administered Under Conditions of Stimulated Gastric Acid Secretion in the Gastric Fistula Dog." *Life Sciences*. 49.14(1991):1047-1052.
Vitale et al. "Succinic and Malic Oxidase in Gastric Hydrochloric Acid Production." *Am. J. Physiol.* 187(Nov. 1956):427-431.
Mashkovsky et al. "Medicaments." Moscow: OOO Novaya Volna, 2001. 1:11.
"Omeprazole: Administration." Gold Standard, 2010.
"Secretory Functions of the Alimentary Tract." *Textbook of Medical Physiology*. Guyton et al., eds. Philadelphia: W. B. Saunders Co. 10th ed. Ch. 64. (2000):738-753.

(56) References Cited

OTHER PUBLICATIONS

*Burger's Medicial Chemistry and Drug Discovery.* Abraham et al., eds. 6th ed. Hoboken, NJ: John Wiley & Sons, Inc. 4(2003):102-115.
MacDonald et al. "Glyceraldehyde Phosphate and Methyl Esters of Succinic Acid." *Diabetes.* 37(1988):997-999.
"Lansoprazole." Gold Standard Inc. (2010).
"Omeprazole." Gold Standard Inc. (2010).
Ranucci et al. "Polymeric Pharmaceutical Excipients." *Pharmaceutical Dosage Forms: Disperse Systems.* New York: Marcel Dekker, Inc. Lieberman et al., eds. 2nd ed. 3(1998):243, 272, 282.
Sherwood. "The Digestive System." *Human Physiology: From Cells to Systems.* Belmont, CA: Brooks/Cole. 5th ed. (2004):591-616.
Wan et al. "Matrix Swelling: A Simple Model Describing Extent of Swelling of HPMC Matrices." *Int. J. Pharmaceutics.* 116(1995):159-168.
The Merck Index Online, "Colloidal Bismuth Subcitrate", CAS Registry No. 57644-54-9, Royal Society of Chemistry, 1 page (2013).
FDA Guidelines for Industry Non-Sterile Semisolid Dosage Forms, 40 pages (May 1997).
International Preliminary Report on Patentability for international application PCT/IB2009/006176 dated Nov. 17, 2010, 6 pages.

* cited by examiner

US 9,278,080 B2

COMPOSITIONS AND METHODS FOR INHIBITING GASTRIC ACID SECRETION

RELATED APPLICATION DATA

This application is a continuation of U.S. Ser. No. 11/191,688, filed Jul. 27, 2005, which is based on and claims the benefit of U.S. Provisional Patent Application No. 60/679,664 filed on May 11, 2005. The disclosure of both of these applications is incorporated herein by reference in their entireties.

FIELD OF THE INVENTION

The present invention relates to novel oral compositions for inhibition of gastric acid secretion comprising a proton pump inhibitor in conjunction with one or more small monocarboxylic, dicarboxylic or tricarboxylic acids in an amount sufficient to activate parietal cells. The present invention further relates to a method of using such compositions to reduce gastric acid secretion in a mammal.

BACKGROUND OF THE INVENTION

A wide number of pathological conditions are characterized by the need to suppress gastric acid secretion. Such conditions include, but are not limited to Zollinger/Ellison syndrome (ZES), gastroesophageal reflux disease (GERD), peptic ulcer disease, duodenal ulcers, esophagitis, and the like. Conditions such as peptic ulcers can have serious complications and represent some of the most prevalent diseases in industrialized nations.

Presently, the main therapies employed in the treatment of GERD and peptic ulcer diseases include agents for reducing the stomach acidity, for example by using the histamine $H_2$-receptor antagonists or proton pump inhibitors (PPIs). PPIs act by inhibiting the parietal cell $H^+/K^+$ ATPase proton pumps responsible for acid secretion from these cells. PPIs, such as omeprazole, and its pharmaceutically acceptable salts are disclosed for example in EP 05129, EP 124495 and U.S. Pat. No. 4,255,431.

PPI agents are acid-labile pro-drugs that are usually administered in enteric-coated granules and are weak bases. Following absorption in the small intestine, PPIs preferentially accumulate within the acid milieu of the acid-secreting parietal cells. The acid environment within the acid milieu of parietal cells causes the conversion of the pro-drugs into the active sulfenamides, which are the active agents that bind and inhibit the parietal cell $H^+/K^+$ ATPase pumps. Thus, pre-activation of parietal cells is required for the conversion of PPIs to its active protonated form. The pre-activation of parietal cells is usually achieved by meal ingestion that initiates gastrin-dependent parietal cell activation. Indeed, patients are instructed to take PPI one hour prior to meal intake in order to ensure that parietal cells are activated when the PPI reaches the parietal cells via blood stream.

Despite their well-documented efficacy, PPIs have notable limitations. The conversion of PPI to its active form requires pre-activation of parietal cells. The pre-activation of parietal cells is normally achieved by ingestion of food. Thus, the PPI must be taken prior to ingestion of food in order to synchronize between the pre-activation of parietal cells and PPI absorption in blood. Furthermore, PPIs have a relatively slow onset of pharmacological action and may require several days to achieve maximum acid suppression and symptom relief, limiting their usefulness in on-demand GERD therapy (Sachs G, Eur J Gastroenterol Hepatol. 2001; 13 Suppl 1:S35-41).

Moreover, PPIs fail to provide 24-h suppression of gastric acid and nocturnal acid breakthrough that leads to heartburn pain in GERD patients and occurs even with twice-daily dosing of PPIs (Tytgat G N, Eur J Gastroenterol Hepatol. 2001; 13 Suppl 1:S29-33; Shaker R. et al., Am. J. of Gastroenterology, 98 (7), 2003). Finally, these drugs exhibit substantial inter-patient variability in pharmacokinetics and may have significant interactions with other drugs (Hatlebakk et al., Clin Pharmacokinet. 1996; 31(5):386-406). Thus, an improvement of PPI-mediated activity is a well-recognized challenge in gastroenterology.

Maleic acid and succinic acid, chemically characterized as four-carbon dicarboxylic acids, are known as powerful stimulants of gastric acid secretion (Teyssen et al., J. Clin Invest. 1999 103(5): 707-713). Teyssen et al. studied the stimulation of gastric acid secretion in fermented alcoholic beverages produced by fermentation (e.g., beer and wine). Interestingly, maleic acid and succinic acid were found to stimulate gastric acid output in humans as that produced by beer, champagne, wine, and pentagastrin (a powerful exogenous stimulus to induce acid secretion), but without gastrin being their mediator of action.

U.S. Pat. No. 5,559,152 discloses that a mixture of succinic acid and citric acid in the dose of 3.5 mg/kg is capable of inducing gastric acid secretion in dogs as reflected by significant reduction in the pH of the gastric juice measured on an empty stomach 40 min following drug administration. This patent further discloses that succinic and citric acid stimulate acid secretion in healthy human volunteers.

Pokrovskiy et al. (Physiologicheskiy Z'urnal 10:1567-1573, 1973) also disclosed that molecules involved in the mitochondrial respiration circle (krebs cycle) such as pyruvate, succinate, alpha-ketoglutarate, malate or glucose may stimulates proton secretion in ex vivo model of frog mucosa.

U.S. Pat. Nos. 6,489,346; 6,645,988; and 6,699,885; to Phillips (jointly the "Phillips patents") disclose pharmaceutical compositions and methods of treating acid-caused gastrointestinal disorders using oral compositions consisting of a PPI, at least one buffering agent and specific parietal cell activators. The parietal cell activators disclosed in the Phillips patents include, for example, chocolate, sodium bicarbonate, calcium, peppermint oil, spearmint oil, coffee, tea and colas, caffeine, theophylline, theobromine and amino acids residues. As indicated in the Phillips patents, all these proposed parietal cell activators induce the release of endogenous gastrin leading to stimulatory effects on acid secretion.

All parietal cell activators taught by the prior art to facilitate PPI activity are either gastrin analogs or parietal cell activators that induce release of endogenous gastrin. Applicants surprisingly discovered compositions and methods of effectively facilitating the inhibitory activity of PPIs in a gastrin-independent manner, without activating the gastrin-histamine pathway. The prior art fails to teach or suggest a gastrin-independent manner of facilitating the inhibitory effect of PPIs.

The development of an effective gastrin-independent treatment for pathologies in which inhibition of gastric acid secretion is required would fulfill a long felt need. Despite the wide-spread use of PPIs, a need still exist for increasing the PPI efficacy, e.g., prolonged effect to control night time acid breakthrough, greater effect at reduced dosage and meal-independent administration. Applicants' invention disclosed herein meets many of these long felt needs.

SUMMARY OF THE INVENTION

It is the object of the present invention to provide PPI-based compositions with enhanced activity in inhibition of gastric acid secretion.

In one embodiment, the present invention relates to compositions comprising a substituted benzimidazole $H^+/K^+$-ATPase proton pump inhibitor (PPI) as a gastric acid secretion inhibitor and one or more saturated or non-saturated small monocarboxylic, dicarboxylic or tricarboxylic acids, salts or derivatives thereof as activators of parietal cells. Preferred acids to be used as parietal cell activators are small monocarboxylic, dicarboxylic or tricarboxylic acid involved in the mitochondrial respiration circle (krebs cycle). Unexpectedly, the compositions of the present invention are capable of enhancing the anti-acid activity of PPI in the stomach. The present compositions may be used for treating a subject suffering from chronic or acute disorders in which suppression of acid secretion in the stomach is required.

The substituted benzimidazole proton pump inhibitors according to the present invention are compounds that inhibit the activity of the $H^+/K^+$-adenosine triphosphatase (ATPase) proton pump in the gastric parietal cells. In its pro-drug form, the PPI is non-ionized and therefore is capable of passing through the cellular membrane of the parietal cells. Once reaching the parietal cells, the non-ionized PPI moves into the acid-secreting portion of activated parietal cells, the secretory canaliculus. The PPI trapped in the canaliculus becomes protonated, thus converted to the active sulfenamide form that can form disulfide covalent bonds with cysteine residues in the alpha subunit of the proton pump, thereby irreversibly inhibiting the proton pump.

The present invention is based on the inventors surprising discovery that small monocarboxylic, dicarboxylic or tricarboxylic acid molecules involved in the mitochondrial respiration circle (krebs cycle) such as maleic acid and succinic acid can enhance the activity of proton pump inhibitors in inhibiting gastric acid secretion. Such small saturated or non-saturated dicarboxylic acids activate parietal cells. Active parietal cells possess acidic pH, which is required for the conversion of the PPI to the active protonated sulfenamide form. Therefore, the synchronized activation of the parietal cells by the small molecules of the present invention maximizes the inhibition of the pumps by the PPI.

The compositions of the present invention exhibit the following advantages over the known PPI-based compositions aimed to reduce gastric acid secretion. The present compositions permit pre-activation of the parietal cells by the parietal cell activator molecules of the present invention instead of food ingestion. Pre-activation of parietal cells by these molecules facilitates the conversion of the PPI to the active sulfenamide form. Furthermore, the present compositions exhibit anti-acid activity in the stomach in a meal-independent manner, since meal is no more required for pre-activation of parietal cells. Thus, the combined active agents of the present compositions provide an effective solution for bed-time PPI administration in GERD patients that are instructed not to ingest food at bed-time.

The compositions according to the present invention may comprise any small monocarboxylic, dicarboxylic or tricarboxylic acids, salts or derivatives thereof in an amount sufficient to activate parietal cells in the gastric lumen. Preferred carboxylic acids are small saturated or non-saturated monocarboxylic, dicarboxylic or tricarboxylic acids involved in krebs cycle. Most preferred small dicarboxylic acids are saturated or non-saturated dicarboxylic or tricarboxylic acids such as maleic acid, succinic acid or citric acid, or any derivative or salts thereof. Also included within the scope of the present invention are other small carboxylic acid molecules involved in krebs cycle such as for example pyruvate, α-ketoglutarate, succinyl-CoA, fumarate, or oxaloacetate.

The compositions according to the present invention are preferably oral compositions, however, parenteral compositions are also included in the scope of the present invention. The active ingredients of the present invention may be formulated in a single oral dosage form, preferably a solid dosage form. In this case, the release of the PPI and the small carboxylic acids is adjusted so as to achieve synchronization between the activation of parietal cells and the absorption of PPI in blood. Thus, in one embodiment the PPI and the parietal cell activators according to the present invention may be formulated as multi-layered tablets, suspension tablets, effervescent tablets, powder, pellets, granules, hard gelatin capsules comprising multiple beads, or soft gelatin capsules containing a lipid-based vehicle. Liquid dosage forms such as suspensions may be used as well.

According to one embodiment, the solid dosage form of the present invention is a capsule or a multi-layered tablet containing PPI particles coated with either enteric pH-dependent release polymers or non-enteric time-dependent release polymers and particles of the parietal cell activators according to the present invention. In order to ensure that the activation of parietal cells by the small carboxylic acids is synchronized with the absorption of the PPI in the proximal part of the small intestine, the single oral dosage form may comprise small carboxylic acids beads coated with a time-dependent release polymer that extends the releasing time in the stomach. Specifically, the delay in the release of small carboxylic acids in the stomach permits the synchronization between the activity of the carboxylic acids as parietal cell activators and the absorption of the PPI in the systemic circulation followed by conversion of the PPI to its protonated form within activated parietal cells.

The active ingredients of the present invention may also be formulated in separate dosage forms. For example, the small carboxylic acids according to the present invention may be formulated in an oral suspension or a solid dosage form such as capsules, tablets, suspension tablets, or effervescent tablets and the PPI may be formulated in a separate solid dosage form, preferably capsules or tablets comprising beads with enteric pH-dependent release polymers or non-enteric time-dependent release polymers. The separate dosage forms may be provided as a kit containing beads of the small carboxylic acids in one dosage form and the beads of PPI in a separate dosage form. In this case, the small carboxylic acids are administered in conjunction with the PPI so that there is at least some chronological overlap in their physiological activity. The PPI and the small carboxylic acids can be administered simultaneously and/or sequentially.

The active ingredients of the present invention may also be formulated in a dosage form suitable for parenteral administration such as intravenous administration and subcutaneous injection. It is also possible that one of the active ingredients is administered orally (such as in tablets or capsules) and the second active ingredient is administered parenterally by intravenous or subcutaneous injection.

In another embodiment, the present invention is directed to a method of treating a subject suffering from a disorder in which suppression of gastric acid secretion is required or a disorder normally treated by suppression of gastric acid secretion. The method comprising administering to the subject a pharmaceutical composition comprising a PPI as a gastric acid secretion inhibitor and one or more small carboxylic acids as an activator of parietal cells.

The compositions of the present invention may be used for preventing or treating pathologies in a mammal in which inhibition of gastric acid secretion is required. Preferably the mammal is human. The compositions of the present invention are effective both in treating the pathologies and in minimizing the risk of development of such pathologies before onset of symptoms.

The pharmaceutical compositions of the present invention may be used in a wide number of pathological conditions that are treated by suppression of gastric acid secretion. Such conditions include, but are not limited to Zollinger/Ellison syndrome (ZES), gastroesophageal reflux disease (GERD), esophagitis, peptic ulcer diseases, duodenal ulcers, gastritis and gastric erosions, dyspepsia, NS/U:1)-induced gastropathy, and the like.

The present invention also includes a pharmaceutical kit, preferably an oral pharmaceutical kit. The kit typically comprises as active ingredients a pharmaceutically effective amount of (i) one or more small carboxylic acids according to the present invention; and (ii) a substituted benzimidazole $H^+/K^+$-ATPase proton pump inhibitor. In one embodiment, the active ingredients are formulated in separate dosage unit forms. The kit may be used to treat or prevent a disorder in a subject in which suppression of gastric acid secretion is required by administering to a subject the active ingredients. The one or more small carboxylic acids are typically administered simultaneously, prior to or following the administration of the PPI.

The present invention also includes an oral pharmaceutical composition comprising as active ingredients a pharmaceutically effective amount of: (i) one or more parietal cell activators in a delayed-release formulation; and (ii) a substituted benzimidazole $H^+/K^+$-ATPase proton pump inhibitor in a delayed-release formulation, wherein the release of the parietal cell activator from the composition is delayed such as to enable synchronization between the activity of the parietal cell activator on parietal cells and the absorption of the PPI in blood. It is preferable that the parietal cell activator will be released prior to the release of the PPI from the composition in order to ensure that the PPI will reach the parietal cells via blood stream when already activated by the parietal cell activator. However, according to other embodiments, the PPI may be released prior to the release of the parietal cell activator in cases where the PPI remains in blood for longer periods to ensure overlap with the activity of the parietal cell activator. The synchronization is essential in order to maximize the inhibition of the $H^+/K^+$-ATPase proton pumps by the PPI. The particles of both PPI and the parietal cell activator may be coated with either enteric-coated polymers (pH-dependent release polymers) or non-enteric-coated polymers (time-dependent release polymers).

These and further embodiments will be apparent from the detailed description and examples that follow.

DETAILED DESCRIPTION OF THE INVENTION

Figure 1:
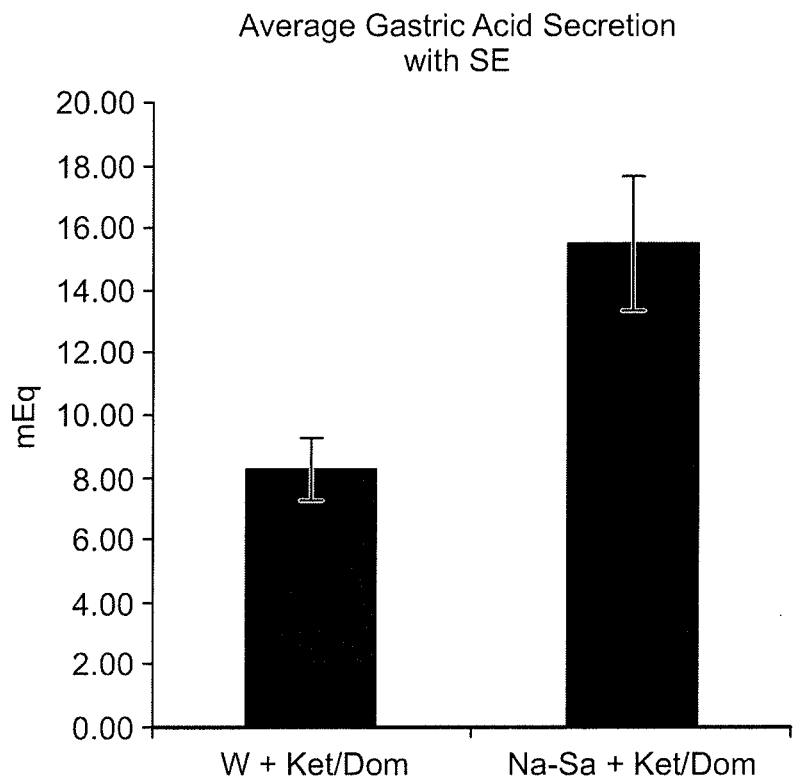
FIG. 1 demonstrates that succinic acid is capable of inducing gastric acid secretion in rats.

Parietal cell activation is required for the conversion of the PPI pro-drug to the active form that acts as an irreversible inhibitor of the gastric $H^+/K^+$-ATPase proton pump. The compositions of the present invention provide a unique combination of active agents that increase the efficacy of the PPI in inhibiting gastric acid secretion without the requirement of food ingestion.

The compositions of the present invention may be used for preventing or treating pathologies in a mammal in which inhibition of gastric acid secretion is required. The compositions of the present invention are effective both in treating the pathologies and in minimizing the risk of development of such pathologies before onset. Such pathologies include for example: reflux esophagitis, gastritis, duodenitis, gastric ulcer and duodenal ulcer. Furthermore, the compositions of the present invention may be used for treatment or prevention of other gastrointestinal disorders where gastric acid inhibitory effect is desirable, e.g. in patients on nonsteroidal anti-inflammatory drugs (NSAID) therapy (including low dose aspirin), in patients with Non Ulcer Dyspepsia, in patients with symptomatic gastro-esophageal reflux disease (GERD), and in patients with gastrinomas. They may also be used in patients in intensive care situations, in patients with acute upper gastrointestinal bleeding, in conditions of pre- and postoperatively to prevent aspiration of gastric acid and to prevent and treat stress ulceration. Further, they may be useful in the treatment of *Helicobacter* infections and diseases related to these. Other conditions well suited for treatment include, but are not limited to Zollinger-Ellison syndrome (ZES), Werner's syndrome, and systemic mastocytosis.

The parietal cell activator according to the present invention is preferably one or more small monocarboxylic, dicarboxylic or tricarboxylic acids, or any active derivative or salt thereof. Preferred acid molecules are small carboxylic acids involved in krebs cycle. Specific preferred acid molecules are saturated aliphatic and non-saturated dicarboxylic acids that may be used as parietal cell activator according to the present invention. Small aliphatic dicarboxylic acids are represented by the general formula: $HO_2C—(CH_2)_n—CO_2H$ (where n=0 to 5). Specific small saturated aliphatic dicarboxylic acids are Oxalic (n=0), Malonic (n=1), Succinic (n=2), Glutaric (n=3), Adipic (n=4) and Pimelic (n=5) Acids. Preferred aliphatic dicarboxylic acids to be used as parietal cell activators according to the present invention are aliphatic dicarboxylic acids having from 2 to 6 carbon atoms, more preferably 4 carbon atoms such as succinic acid. Preferred non-saturated dicarboxylic acids to be used as parietal cell activators according to the present invention are the four carbon maleic acid and fumaric acid. Instead of the free dicarboxylic acids, corresponding dicarboxylic acid derivatives may be used, for example dicarboxylic acid esters, amides, halides, or dicarboxylic anhydrides. Also included within the scope of the present invention are small carboxylic acid molecules involved in the mitochondrial respiration circle (krebs cycle) such as for example pyruvate, citrate, fumarate, α-ketoglutarate, succinyl-CoA or oxaloacetate.

The compositions of the present invention comprise one or more small carboxylic acids or an analog thereof in an effective amount to achieve a pharmacological effect on the parietal cells without undue adverse side effects. The standard approximate amount of the small carboxylic acids present in the compositions is preferably in an amount of 1-2500 mg, more preferably 10-1000 mg, and most preferably 50-400 mg.

In one preferred embodiment, the composition of the present invention comprises one or more aliphatic tricarboxylic acids, preferably citric acid in combination with the one or more dicarboxylic acids. The standard approximate amount of one or more tricarboxylic acids present in the compositions is preferably in an amount of 1-1000 mg, more preferably 10-1000 mg, and most preferably 50-200 mg.

The compositions of the present invention further comprise a PPI that acts as an irreversible inhibitor of the gastric $H^+/K^+$-ATPase proton pump. The PPI used in the present invention can be any substituted benzimidazole compound having $H^+/K^+$-ATPase inhibiting activity. For the purposes of this invention, the term "PPI" shall mean any substituted benzimidazole possessing pharmacological activity as an inhibitor of $H^+/K^+$-ATPase, including, but not limited to, omeprazole, lansoprazole, pantoprazole, rabeprazole, dontoprazole, perprazole (s-omeprazole magnesium), habeprazole, ransoprazole, pariprazole, tenatoprazole and leminoprazole in neutral form or a salt form, a single enantiomer or isomer or other derivative or an alkaline salt of an enantiomer of the same.

Examples of gastric $H^+/K^+$-ATPase proton pump inhibitors that may be used in the present invention are disclosed for example in U.S. Pat. No. 6,093,738 that describes novel thiadiazole compounds that are effective as proton pumps inhibitors. European Patent Nos. 322133 and 404322 disclose quinazoline derivatives, European Patent No. 259174 describes quinoline derivatives, and WO 91/13337 and U.S. Pat. No. 5,750,531 disclose pyrimidine derivatives, as proton pump inhibitors. Suitable proton pump inhibitors are also disclosed for example in EP-A1-174726, EP-A1-166287, GB 2 163 747 and WO90/06925, WO91/19711, WO91/19712, WO94/27988 and WO95/01977.

In a non-limiting embodiment, the ratio between the small carboxylic acid molecules, or salts thereof, and the PPI are about 20:1 to about 1:5.

The compositions of the present invention are preferably suitable for oral administration. The PPI particles in the oral compositions according to the present invention may be either coated or non-coated. The preparation of enteric-coated particles comprising a PPI such as Omeprazole is disclosed for example in U.S. Pat. Nos. 4,786,505 and 4,853,230.

The compositions of the present invention comprise a PPI in an effective amount to achieve a pharmacological effect or therapeutic improvement without undue adverse side effects. A therapeutic improvement includes but is not limited to: raising of gastric pH, reduced gastrointestinal bleeding, or improvement or elimination of symptoms. According to a preferred embodiment, the typical daily dose of the PPI varies and will depend on various factors such as the individual requirements of the patients and the disease to be treated. In general, the daily dose of PPI will be in the range of 1-400 mg. A preferred standard approximate amount of a PPI present in the composition is typically about 20-40 mg of omeprazole, about 30 mg lansoprazole, about 40 mg pantoprazole, about 20 mg rabeprazole, and the pharmacologically equivalent doses of the following PPIs: habeprazole, pariprazole, dontoprazole, ransoprazole, perprazole (s-omeprazole magnesium), tenatoprazole and leminoprazole.

The active ingredients of the present invention are preferably formulated in a single oral dosage form containing all active ingredients. The compositions of the present invention may be formulated in either solid or liquid form. It is noted that solid formulations are preferred in view of the improved stability of solid formulations as compared to liquid formulations and better patient compliance.

In one embodiment, the PPI particles and one or more small carboxylic acids are formulated in a single solid dosage form such as multi-layered tablets, suspension tablets, effervescent tablets, powder, pellets, granules or capsules comprising multiple beads. In another embodiment, the active agents may be formulated in a single liquid dosage form such as suspension containing all active ingredients or dry suspension to be reconstituted prior to use.

The acid-labile PPI particles in the present composition are preferably formulated as enteric-coated delayed-release granules in order to avoid contact with the gastric juice. However, the parietal cell activator of the present invention may be formulated either in an immediate-release formulation to enable fast parietal cell activation, or in a delayed-release formulation to better synchronize between the biological activity of the parietal cell activator and the PPI on parietal cells. In this case, particles of both PPI and the parietal cell activator are coated with either enteric-coated polymers (pH-dependent release polymers) or non-enteric-coated polymers (time-dependent release polymers). For example, if coated PPI particles are used resulting in delayed absorption in blood, it is desirable that the parietal cell activator particles be coated as well to delay its release and absorption. In one specific embodiment, the PPI particles are coated with a thick non-enteric-coated layer so as the release of the PPI is preferably delayed by between 40-100 min, more preferably 40-80 min, most preferably 60-80 min, and the parietal cell activator particles are coated with a thin non-enteric-coated polymer layer so as the release of the parietal cell activator is synchronized with the release of the PPI and preferably delayed by 20-80 min, and most preferably by 30-60 min. These conditions permit pre-activation of the parietal cells by the parietal cell activator prior to the achievement of a pharmacological PPI plasma concentration.

Non-limiting examples of suitable pH-dependent enteric-coated polymers to be used in the present invention are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark Eudragit L 100-55. This coating can be spray coated onto the substrate.

Non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

The erosion properties of the polymer in the stomach resulting from the interaction of fluid with the surface of the dosage form are determined mainly by the polymer molecular weight and the drug/polymer ratio. In order to ensure a delay of between about 10 min to about 60 min in the release of the parietal cell activator and the PPI, it is recommended that the molecular weight of the polymer be in the range from about $10^5$ to about $10^7$ gram/mol. Furthermore, it is recommended that the ratio between the parietal cell activator and polymer or PPI and polymer be in the range of about 2:3 to about 9:1, preferably about 3:2 to 9:1, and most preferably about 4:1 to 9:1.

Suitable non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the Eudragit brand polymers. Other film-forming materials may be used alone or in combination with each other or with the ones listed above. These other film forming materials generally include poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials which are suitable for making the time-dependent release coating of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer.

In one specific example, the composition of the present invention is formulated as a single dosage form comprising multiple beads contained in hard gelatin capsules. The capsules contain mixed population of beads selected from: beads comprising enteric-coated PPI or beads comprising PPI coated with time-dependent release polymer, and beads comprising one or more small carboxylic acids coated with either hydroxypropyl methylcellulose or alginate. The rate of the carboxylic acids release is determined by the thickness and the erosion rate of the hydroxypropyl methylcellulose.

In yet another example, the compositions of the present invention are formulated as press-coat or double-layered tablets comprising enteric-coated PPI in one layer and small carboxylic acids coated with hydroxypropyl methylcellulose in a second layer.

In a further example, the compositions of the present invention may be formulated as two layer non-aqueous semi-solid fill into hard gelatin capsules in which the PPI is solubilized in a lipid base (non-aqueous, quick release) which is liquid above room temperature but forms a semi-solid on cooling and can therefore be filled into hard gelatin capsules.

The active ingredients of the present invention may be formulated in a multiple oral dosage forms in which the parietal cell activator is administered in a separate dosage form but in conjugation with the PPI. For example, the parietal cell activator may be formulated in oral suspension or a solid dosage form such as capsules, tablets, suspension tablets, or effervescent tablets and the PPI may be formulated in a separate solid dosage form, preferably enteric-coated beads or time-dependent release beads contained in capsules or tablets.

When using multiple oral dosage forms, the parietal cell activator can be administered before, simultaneously with, or after the PPI. In sequential administration, there may be some substantial delay (e.g., minutes or even few hours) between the administration of the parietal cell activator and the PPI as long as the parietal cell activator has exerted some physiological effect when the PPI is administered or becomes active. In a preferred embodiment, the PPI administered is in the enteric-coated or the time-dependent release form. According to this embodiment, it is preferable that the PPI administration precedes the parietal cell activator administration in order to ensure that the PPI absorbed in the proximal part of the small intestine will be available for inhibiting the H+/K+-ATPase pumps while the parietal cell activator is still active in the parietal cells.

It is also possible to add buffering agents to the formulation in order to facilitate the release of the PPI from the enteric-coated pellets, thereby enhancing the absorption of the PPI in blood. Specifically, a buffering agent such as for example sodium bicarbonate may be added in an amount sufficient to provide a pH above 5 in the stomach. For example, between 300 to 2,000 mg of sodium bicarbonate may be added to the formulation. If fast absorption of PPI in blood is required, it is possible to use non-enteric PPI pellets in the present formulations. In this case, the stability of the PPI in the stomach will be preserved due to the buffering agent that provides a pH above 5 in the stomach. Fast absorption of PPI in blood is especially important in cases where the parietal cell activators possess direct activity on parietal cells via the gastric lumen or in cases where the parietal cell activators are absorbed to the systemic circulation via the stomach. In this case, it is recommended to extend the retention of the parietal cell activators in the stomach in order to permit local activity, or absorption via the stomach.

Prolonging the retention time of the parietal cell activator in the stomach is possible for example by using dosage forms that unfold rapidly within the stomach to a size that resists gastric emptying. Such systems retain their integrity for an extended period and will not empty from the stomach at all until breakdown into small pieces occurs. Caldwell (Caldwell, L. J., Gardener, C. R., Cargill, R. C. (1988), U.S. Pat. No. 4,767,627) describes a cross shaped device made of erodible polymer and loaded with drug which is folded and inserted into a hard gelatin capsule. Following oral administration the gelatin shell disintegrates and the folded device opens out. With a minimum size of 1.6 cm and a maximum size of 5 cm it will not pass from the stomach through the pylorus until the polymer erodes to the point where the system is sufficiently small that it can be passed from the stomach.

An alternative approach to prolong the retention time of the parietal cell activator in the stomach is to use a hydrophilic erodible polymer system such as Poly(ethylene oxide) (Polyox) and Hydroxypropyl-methylcellulose (HPMC) that is of a convenient size for administration to humans. On imbibing fluid the system swells over a short period of time to a size that will encourage prolonged gastric retention, allowing sustained delivery of contained drug to absorption sites in the upper gastrointestinal tract. Because these systems are made of an erodible and hydrophilic polymer or polymer mixture, they readily erode over a reasonable time period to pass from the stomach. The time period of expansion is such that this will not occur in the esophagus and if the system passes into the intestine in a partially swollen state, the erodibility and elastic nature of the hydrated polymer will eliminate the chance of intestinal obstruction by the system.

The active ingredients of the present invention may be incorporated within inert pharmaceutically acceptable beads. In this case, the drug(s) may be mixed with further ingredients prior to being coated onto the beads. Ingredients include, but are not limited to, binders, surfactants, fillers, disintegrating agents, alkaline additives or other pharmaceutically acceptable ingredients, alone or in mixtures. Binders include, for example, celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants include pharmaceutically acceptable non-ionic or ionic surfactants. An example of a suitable surfactant is sodium lauryl sulfate.

The particles may be formed into a packed mass for ingestion by conventional techniques. For instance, the particles may be encapsulated as a "hard-filled capsule" using known encapsulating procedures and materials. The encapsulating material should be highly soluble in gastric fluid so that the particles are rapidly dispersed in the stomach after the capsule is ingested.

In another embodiment, the active ingredients of the present invention are packaged in compressed tablets. The term "compressed tablet" generally refers to a plain, uncoated tablet for oral ingestion, prepared by a single compression or by pre-compaction tapping followed by a final compression. Such solid forms can be manufactured as is well known in the art. Tablet forms can include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmaceutically compatible carriers. The manufacturing processes may employ one, or a combination of, four established methods: (1) dry mixing; (2) direct compression; (3) milling; and (4) non-aqueous granulation. Lachman et al., The Theory and Practice of Industrial Pharmacy (1986). Such tablets may also comprise film coatings, which preferably dissolve upon oral ingestion or upon contact with diluent.

In another alternative, the compositions of the present invention are formulated in compressed forms, such as suspension tablets and effervescent tablets, such that upon reaction with water or other diluents, the aqueous form of the composition is produced for oral administration. These forms are particularly useful for medicating children and the elderly and others in a way that is much more acceptable than swallowing or chewing a tablet. The present pharmaceutical tablets or other solid dosage forms disintegrate the alkaline agent with minimal shaking or agitation.

The term "suspension tablets" as used herein refers to compressed tablets which rapidly disintegrate after they are placed in water, and are readily dispersible to form a suspension containing a precise dosage of the PPI and the parietal cell activator. To achieve rapid disintegration of the tablet, a disintegrant such as croscarmellose sodium may be added to the formulation. The disintegrant may be blended in compressed tablet formulations either alone or in combination with microcrystalline cellulose, which is well known for its ability to improve compressibility of difficult to compress tablet materials. Microcrystalline cellulose, alone or co-processed with other ingredients, is also a common additive for compressed tablets and is well known for its ability to improve compressibility of difficult to compress tablet materials. It is commercially available under the Avicel trademark.

The suspension tablet composition may, in addition to the ingredients described above, contain other ingredients often used in pharmaceutical tablets, including flavoring agents, sweetening agents, flow aids, lubricants or other common tablet adjuvants, as will be apparent to those skilled in the art. Other disintegrants, such as crospovidone and sodium starch glycolate may be employed, although croscarmellose sodium is preferred.

In addition to the above ingredients, the oral dosage forms described above may also contain suitable quantities of other materials, e.g. diluents, lubricants, binders, granulating aids, colorants, flavorants and glidants that are conventional in the pharmaceutical art. The quantities of these additional materials will be sufficient to provide the desired effect to the desired formulation. Specific examples of pharmaceutically acceptable carriers and excipients that may be used to formulate oral dosage forms are described in the Handbook of Pharmaceutical Excipients, American Pharmaceutical Association (1986), incorporated by reference herein.

For parenteral administration, the active ingredients are administered either by intravenous, subcutaneous or intramuscular injection, in compositions with pharmaceutically acceptable vehicles or carriers. For administration by injection, it is preferred to use the active ingredients in solution in a sterile aqueous vehicle, which may also contain other solutes such as buffers or preservatives as well as sufficient quantities of pharmaceutically acceptable salts or of glucose to make the solution isotonic with respect to blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, and preservatives, and optionally, coloring agents, fragrances, flavors, sweeteners, and other pharmacologically active agents which are known in the art.

The dosage of the small carboxylic acid molecules of the present invention may be in the range from about 1 to 100 mg per human adult by parenteral administration per day in multiple dose, depending upon the type of disease, the severity of condition to be treated, and the like.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Stimulation of Gastric Acid Secretion Following Oral Administration of Sodium Succinate in Rats Rats were administered (per os) with 15 mg/kg of sodium succinate using gavage. 30 minutes later the rats were anesthetized with ketamine/domitor and the pylorus was ligated. Following additional 60 min, gastric juice was collected from the gastric lumen. Acid output was determined by titration with NaOH. Total acid output expressed in mEq HCl was calculated by multiplying the sample volume by the acid concentration. Results are expressed as means±SEM of 12 animals from each experimental group. As demonstrated in FIG. 1, oral administration of sodium succinate significantly enhanced gastric acid secretion in pylorus-ligated rats.

Example 2

Succinic Acid is Capable of Enhancing the Inhibitory Effect of Pantoprazole on Gastric Acid Secretion To study the effect of succinic acid on the inhibition of gastric acid secretion by pantoprazole, an experimental model of conscious pylorus-ligated rats was used. This experimental model permits the analysis of the effect of drugs on gastric acid secretion in conscious animals and avoids the effect of anesthesia on gastric acid secretion. Pantoprazole alone (10 mg/ml) and in combination with succinic acid (15 mg/ml) were administered by oral gavage. Water was administered as a placebo. 15 minutes later the animals were anesthetized using anesthetic gas machine for a short period (5 minutes) that is sufficient to perform the pylorus ligation procedure and to close the abdomen. The animals were then placed back into its cage for additional 90 min after which the animals were sacrificed. The ligature was placed around the esophagus, the stomach removed and gastric content was collected. Following centrifugation, the gastric output and the pH of the gastric juice samples was determined. Data is presented as mean±SD of gastric output and pH values. The number of animals is 4-8 in each experimental group.

Figure 2:
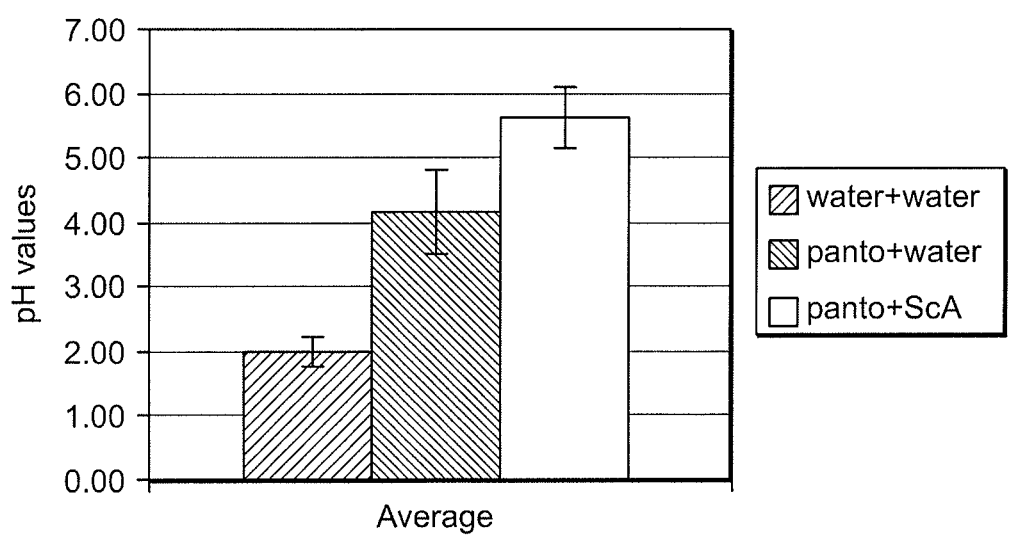
FIG. 2 demonstrates that the administration of pantoprazole (panto) with succinic acid (ScA) resulted in higher pH values in the gastric juice samples as compared to pantoprazole alone.
Figure 3:
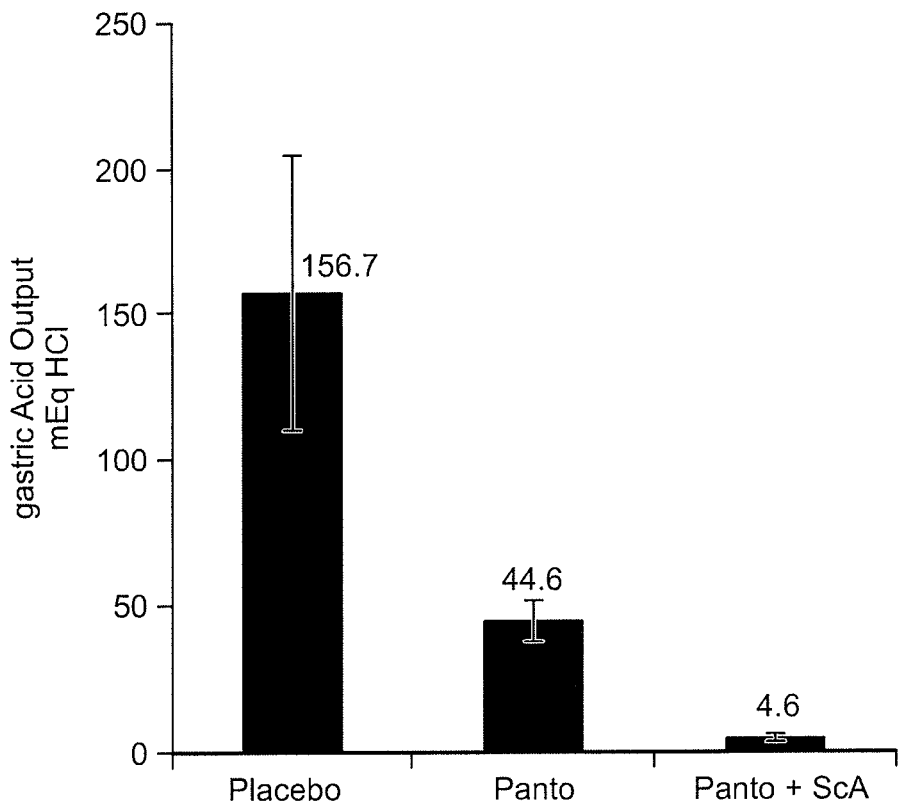
FIG. 3 demonstrates that the administration of pantoprazole with succinic acid (panto-ScA) resulted in lower values of gastric output in the stomach as compared to pantoprazole alone (panto).
Figure 4:
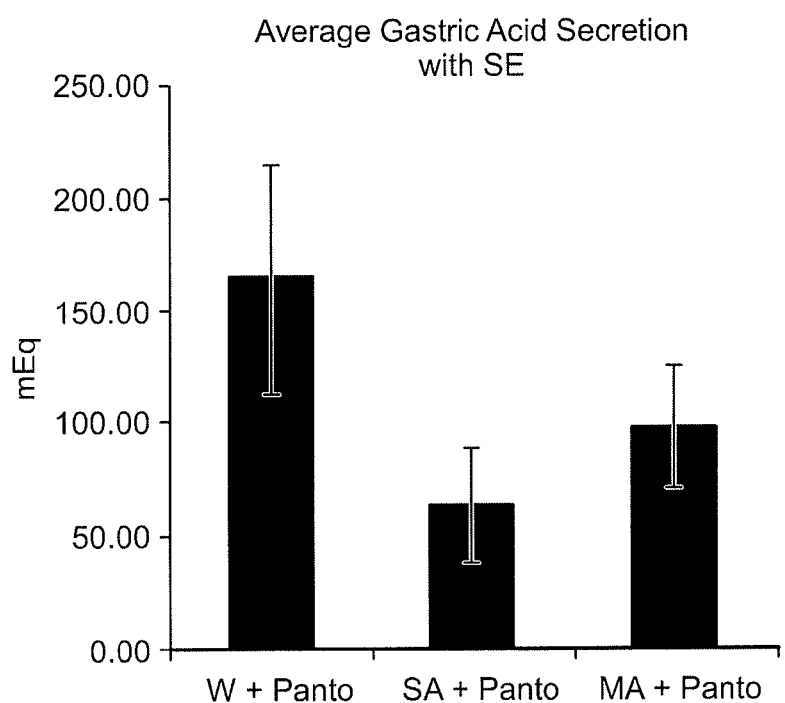
FIG. 4 demonstrates that both succinic and maleic acids may facilitate the effect of Pantoprazole on gastric acid secretion.

As can be seen in FIG. 2, the administration of pantoprazole (panto) with succinic acid (ScA) resulted in higher pH values in the gastric juice samples as compared to pantoprazole alone. FIG. 3 further demonstrates that the administration of pantoprazole with succinic acid resulted in lower values of gastric output in the stomach as compared to pantoprazole alone. These results indicate that succinic acid increases the efficacy of pantoprazole in inhibiting gastric acid secretion. As shown in FIG. 4, maleic acid (14.7 mg/kg) also enhanced the inhibitory effect of pantoprazole (3 mg/kg) on gastric acid secretion.

Figure 5:
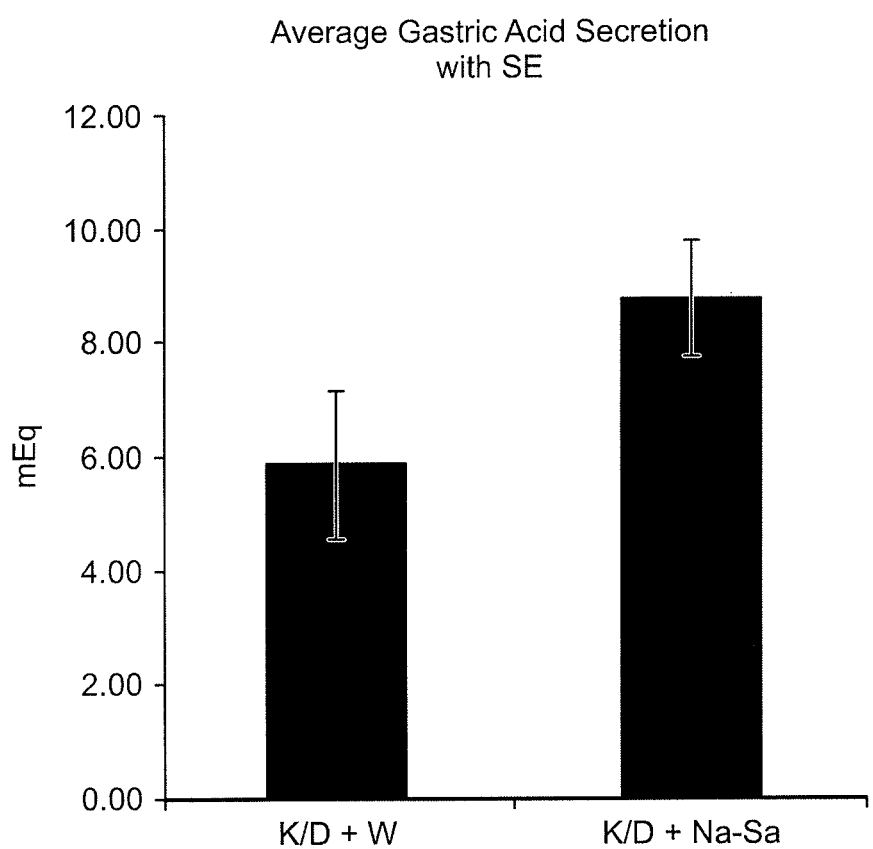
FIG. 5 demonstrates that succinic acid is capable of inducing gastric acid secretion when administered to pylorus-ligated rats.

The possibility that succinic acid induces gastric acid secretion via local effect on the gastric lumen was tested in animals in which sodium succinate was administered after the ligation of the pylorus. In these conditions, sodium succinate can exert local effect within the stomach. As demonstrated in FIG. 5, sodium succinate is capable of inducing acid secretion if administered after ligation, probably via local effect on the gastric lumen. It is possible, however, that succinic acid was absorbed to the systemic circulation via the gastric lumen.

Example 3

Oral Formulations Comprising a Proton Pump Inhibitor (PPI) and Succinic Acid

Hard Gelatin Capsules

Hard gelatin capsules may contain a mixed granules population of succinic acid (ScA) and PPI. ScA granules are in an immediate release or delayed release formulation and PPI is formulated as enteric-coated granules or time-dependent release coating (delayed release). Granules may be packed into a hard gelatin capsule in an amount corresponding to 40 mg PPI and 200 mg ScA per capsule.

A) Immediate Release ScA Formulation:
    40 mg enteric-coated (Eudragit) or time-dependent release coated (HPMC)
    PPI granules
    200 mg ScA granules-
    diluent- B) Delayed Release ScA Formulation:
    40 mg enteric-coated or time-dependent release coated PPI granules 200 mg ScA granules
    (HPMC coated)
    diluent- For the delayed release ScA formulation, ScA solution is sprayed on inert beads in a fluid bed apparatus. After drying, the ScA beads are further coated with hydroxypropyl methylcellulose (HPMC) to form the final granules. The rate of ScA release is determined by the thickness and erosion rate of the HPMC layer. ScA is aimed to be released from the coated beads 10 min following administration.

Tablets or Caplets

The pharmaceutical composition may be in the form of tablet or more preferably caplet. The caplet contains a mixed granules population of ScA (immediate release or delayed release, as mentioned above), enteric-coated or time-dependent release coated PPI (stable under compression pressure) and a wide variety of conventional tableting aid agents to be compressed into a caplet formulation.

Minitabs in Hard Gelatin Capsule (Gastric Retentive Dosage Form)

ScA are granulated with a combination of Polyox WSR N60 and HPMC K100M. These granules are further combined with lactose and HPMC and later on compressed into mini-tabs with the ability of fast swelling into size, big enough to enable gastric retention. The polymeric matrix controls the ScA release into the stomach.

The ScA mini-tabs are mixed with enteric-coated PPI pellets and filled into hard gelatin capsules. Following disintegration of the capsules gelatinic body, the PPI pellets pass though the stomach to the duodenum, where the enteric coat will dissolve. The ScA mini-tabs remain in the stomach and slowly release their content in a controlled release gastro retentive manner.

Press Coated Tablet

The tablet's internal core is composed of ScA combined with a mixture of hydrogels aimed for controlled release and prompt swelling of the dosage form. The expanded core has gastro-retentive properties. Mixtures of gums like: xanthan gum, gellan gum, together with cellulose derivatives such as sodium carboxymethylcellulose or HPMC may be applied.

The core is further coated with an external layer composed of enteric-coated PPI pellets (stable under compression pressure) together with appropriate filler, which disintegrates immediately after digestion and promptly releases the PPI. The final product is a tablet composed of an internal controlled-release core of ScA and an outer layer, immediate release type with the enteric-coated or time-dependent release coated PPI.

Pulsatile Release Dosage Forms

Hard gelatin capsules are filled with:
a) ScA granules, combined with HPMC K100M and Vitamin E-TPGS combined together with sodium chloride (osmotic agent, to attract water into the capsule).
b) Expansion layer with a mixture of hydrogels like Polyox WSR N60, carboxymethylcellulose.
c) Enteric-coated or time-dependent release coated PPI pellets.
d) Optionally, granules of between 300 to 2,000 mg of sodium bicarbonate may be added.

The capsule body is coated with non-soluble coating layer such as ethyl cellulose or cellulose acetate. After digestion, the mid layer will get hydrated and expanded, to prompt the release of the PPI pellets into the stomach. The ScA will remain in the capsule body, which will act as a gastro retentive controlled release dosage form, while the release is controlled by the hydrogel layer.

Powder for Oral Suspension

Powder for oral suspension is comprised of ScA and enteric-coated or time-dependent release coated PPI granules. ScA granules may be in immediate release or delayed release formulation (as mentioned above). PPI are formulated as enteric-coated or time-dependent release coated granules (delayed release). The composition comes in individual packets to be constituted with water. When mixed with water, powder becomes a uniform liquid suspension.

Injectable Preparation

A PPI and succinic acid liquid solution is prepared by dissolving succinic acid in phosphate-buffered saline. To prepare a physiological phosphate-buffered saline solution for dissolution of PPI and succinic acid, a concentrated (20 times) solution of phosphate buffered saline (PBS) is diluted to obtain a 1× solution. The 20 times PBS solution is prepared by dissolving the following reagents in sufficient water to make 1,000 ml of solution: sodium chloride, 160 grams; potassium chloride, 4.0 grams; sodium hydrogen phosphate, 23 grams; potassium dihydrogen phosphate, 4.0 grams; and optionally phenol red powder, 0.4 grams. The PBS solution is then sterilized by autoclaving at 15 pounds of pressure for 15 minutes and is diluted with additional sterile water to a 1 times concentration prior to dissolution of the PPI and succinic acid. To prepare a dose form for intravenous administration, PPI and succinic acid are dissolved in 1 times PBS at concentrations of 0.2 mg and 1 mg/ml, respectively, and the resulting solution (200 ml) is dispensed into sealable translucent plastic bags for use in intravenous administration of the compounds. These steps are performed under sterile conditions.

It will be appreciated by a person skilled in the art that the present invention is not limited by what has been particularly shown and described hereinabove. Rather, the scope of the invention is defined by the claims that follow.

The invention claimed is:

1. A pharmaceutical composition comprising active ingredients in a solid dosage form suitable for oral administration, wherein the active ingredients of said composition consist of a pharmaceutically effective amount of: (i) a parietal cell activator, wherein the parietal cell activator is one or more small carboxylic acid molecules or any salts thereof which activate parietal cells without activating the gastrin-histamine pathway, wherein the small carboxylic acid molecules or any salts thereof are saturated or non-saturated monocarboxylic, dicarboxylic or tricarboxylic acid molecules or any salts thereof involved in the mitochondrial respiration circle (Krebs cycle) having between three to six carbon atoms selected from the group consisting of pyruvate, alpha-ketoglutarate, succinyl-CoA, and any salts thereof; and (ii) an irreversible gastric $H^+/K^+$-ATPase proton pump inhibitor (PPI), wherein the PPI is formulated as particles that are enteric coated, wherein the solid dosage form is suitable for administration to a human patient, wherein the solid dosage form disintegrates in the stomach, wherein the PPI is formulated for absorption in the small intestine and the carboxylic acid molecules or any salts thereof is in a form for release in the stomach in an amount sufficient to activate parietal cells located in the gastric lumen of the human patient, wherein the one or more small carboxylic acid molecules or salts thereof are formulated as particles that are in a delayed release formulation to synchronize activation of parietal cells in the gastric lumen with the absorption of the PPI in the small intestine to increase the effectiveness of the PPI, wherein the amount of the small carboxylic acid molecules or any salts thereof is between 50 and 2500 mg and the amount of PPI is between 1 and 400 mg, wherein the weight ratio between the one or more small carboxylic acid molecules or any salts thereof and the PPI is about 20:1 to about 1:5, wherein the carboxylic acid molecules or any salts thereof in conjunction with the PPI reduces gastric acid secretion in the stomach, and wherein the active ingredients are formulated in a single unit oral dosage form selected from the group consisting of multi-layered tablets, powders, pellets, granules, capsules, press-coat tablets, capsules comprising multiple beads, multi-particulate capsules, and suspension tablets.

2. The composition of claim 1, wherein the one or more small carboxylic acid molecules or any salts thereof are granulated into beads which are compressed into mini-tabs and mixed with enteric-coated PPI pellets in hard or soft gelatin capsules or wherein the composition comprises multiple beads of the one or more small carboxylic acid molecules or any salts thereof and the PPI in hard gelatin capsule.

3. The composition of claim 1, wherein the PPI is selected from the group consisting of: rabeprazole; omeprazole; esomeprazole; lansoprazole; pantoprazole; leminoprazole; tenatoprazole; a single enantiomer of rabeprazole, omeprazole, esomeprazole, lansoprazole, pantoprazole, leminoprazole, or tenatoprazole; an alkaline salt of rabeprazole, omeprazole, esomeprazole, lansoprazole, pantoprazole, leminoprazole, or tenatoprazole; a pro-drug form of rabeprazole, omeprazole, esomeprazole, lansoprazole, pantoprazole, leminoprazole, or tenatoprazole; and mixtures thereof.

4. A pharmaceutical kit comprising active ingredients for administration to a human patient wherein the active ingredients consist of a pharmaceutically effective amount of: (i) a parietal cell activator, wherein the parietal cell activator is one or more small carboxylic acid molecules or any salts thereof which activate parietal cells without activating the gastrin-histamine pathway, wherein the small carboxylic acid molecules or any salts thereof are saturated or non-saturated monocarboxylic, dicarboxylic or tricarboxylic acid molecules or any salts thereof involved in the mitochondrial respiration circle (Krebs cycle) having between three to six carbon atoms selected from the group consisting of pyruvate, alpha-ketoglutarate, succinyl-CoA, and any salts thereof; and (ii) an irreversible gastric $H^+/K^+$-ATPase proton pump inhibitor (PPI), wherein the PPI is formulated as particles that are enteric coated, wherein the kit comprises a dosage form suitable for administration to a human patient that disintegrates in the stomach, wherein the PPI is formulated for absorption in the small intestine and the carboxylic acid molecules or any salts thereof are in a form for release in the stomach in an amount sufficient to activate parietal cells located in the gastric lumen of the human patient, wherein the one or more small carboxylic acid molecules or salts thereof are formulated as particles that are in a delayed release formulation to synchronize activation of parietal cells in the gastric lumen with the absorption of the PPI in the small intestine to increase the effectiveness of the PPI, wherein the amount of the small carboxylic acid molecules or any salts thereof is between 50 and 2500 mg and the amount of PPI is between 1 and 400 mg, wherein the weight ratio between the one or more small carboxylic acid molecules or any salts thereof and the PPI is about 20:1 to about 1:5, wherein the carboxylic acid molecules or any salts thereof in conjunction with the PPI reduces gastric acid secretion in the stomach, and wherein the active ingredients are formulated in a single unit oral dosage form selected from the group consisting of multi-layered tablets, powders, pellets, granules, capsules, press-coat tablets, capsules comprising multiple beads, multi-particulate capsules, and suspension tablets.

5. A method of reducing gastric acid secretion in a human patient, the method comprising administering to the patient an effective amount of the pharmaceutical composition of claim 1.

6. The method of claim 5, wherein the human patient has a disorder selected from the group consisting of: esophagitis, gastritis, duodenitis, peptic ulcer, duodenal ulcer, pathologies associated with nonsteroidal anti-inflammatory drugs (NSAID), non-ulcer Dyspepsia, gastro-esophageal reflux disease, gastrinomas, acute upper gastrointestinal bleeding, stress ulceration, *Helicobacter pylori* infections, Zollinger-Ellison syndrome (ZES), Werner's syndrome, and systemic mastocytosis.

7. The method of claim 5, wherein the release of the one or more small carboxylic acid molecules or any salts thereof in the stomach is delayed by between 10 and 60 minutes to synchronize the release with absorption of the PPI in the blood.

8. A pharmaceutical composition comprising active ingredients in a solid dosage form suitable for oral administration selected from the group consisting of capsules and tablets to a human patient, wherein the active ingredients of the capsules and tablets consist of a pharmaceutically effective amount of: (i) a parietal cell activator, wherein the parietal cell activator is one or more small carboxylic acid molecules or any salts thereof which activate parietal cells without activating the gastrin-histamine pathway, wherein the small carboxylic acid molecules or any salts thereof are saturated or non-saturated monocarboxylic, dicarboxylic or tricarboxylic acid molecules or any salts thereof involved in the mitochondrial respiration circle (Krebs cycle) having between three to six carbon atoms selected from the group consisting of pyruvate, alpha-ketoglutarate, succinyl-CoA, and any salts thereof; and (ii) an irreversible gastric $H^+/K^+$-ATPase proton pump inhibitor (PPI), wherein the PPI is formulated as particles that are enteric coated and is selected from the group consisting of: rabeprazole, omeprazole, esomeprazole, isomeprazole, lansoprazole, pantoprazole, leminoprazole, tenatoprazole, single enantiomers thereof, alkaline salts thereof, pro-drug forms thereof, and mixtures thereof, wherein the PPI is formulated for absorption in the small intestine and the carboxylic acid molecules or any salts thereof is in a form for release in the stomach in an amount sufficient to activate parietal cells located in the gastric lumen of the human patient, wherein the one or more small carboxylic acid molecules or salts thereof are formulated as particles that are in a delayed release formulation to synchronize activation of parietal cells in the gastric lumen with the absorption of the PPI in the small intestine to increase the effectiveness of the PPI, wherein the amount of the small carboxylic acid molecules or any salts thereof is between 50 and 2500 mg and wherein the amount of PPI is between 1 and 400 mg, wherein the weight ratio between the one or more small carboxylic acid molecules or any salts thereof and the PPI is about 20:1 to about 1:5, wherein the carboxylic acid molecules or any salts thereof enhance the activity of the PPI at inhibiting gastric acid secretion in the stomach, and wherein the active ingredients are formulated in a single unit oral dosage form selected from the group consisting of multi-layered tablets, powders, pellets, granules, capsules, press-coat tablets, capsules comprising multiple beads, multi-particulate capsules, and suspension tablets.

9. The composition of claim 1 further comprising one or more additional small carboxylic acid molecules or any salts thereof selected from the group consisting of maleic acid, citric acid, fumarate, and oxaloacetate.

10. The kit of claim 4 further comprising one or more additional small carboxylic acid molecules or any salts thereof selected from the group consisting of maleic acid, citric acid, fumarate, and oxaloacetate.

11. The composition of claim 8 further comprising one or more additional small carboxylic acid molecules or any salts thereof selected from the group consisting of maleic acid, citric acid, fumarate, and oxaloacetate.

* * * * *